(12) United States Patent
Burriesci et al.

(10) Patent No.: US 10,357,358 B2
(45) Date of Patent: Jul. 23, 2019

(54) HEART VALVE PROSTHESIS

(75) Inventors: Gaetano Burriesci, London (GB);
Alexander M. Seifalian, London (GB);
Constantinos Zervides, Limassol (CY)

(73) Assignee: UCL BUSINESS PLC, London (GB)

(*) Notice: Subject to any disclaimer, the term of this patent is extended or adjusted under 35 U.S.C. 154(b) by 423 days.

(21) Appl. No.: 13/262,539

(22) PCT Filed: Mar. 30, 2010

(86) PCT No.: PCT/GB2010/000627
§ 371 (c)(1),
(2), (4) Date: Dec. 19, 2011

(87) PCT Pub. No.: WO2010/112844
PCT Pub. Date: Oct. 7, 2010

(65) Prior Publication Data
US 2012/0165929 A1    Jun. 28, 2012

(30) Foreign Application Priority Data

Mar. 30, 2009 (GB) .................................. 0905444.6

(51) Int. Cl.
*A61F 2/24* (2006.01)
*A61F 2/95* (2013.01)

(52) U.S. Cl.
CPC .... *A61F 2/2418* (2013.01); *A61F 2002/9522* (2013.01); *A61F 2220/005* (2013.01); *A61F 2230/005* (2013.01); *A61F 2230/0054* (2013.01)

(58) Field of Classification Search
CPC .... A61F 2/2442; A61F 2/2445; A61F 2/2463; A61F 2/06; A61F 2/07; A61F 2/24; A61F 2/2418; A61F 2002/952; A61F 2/91
(Continued)

(56) References Cited

U.S. PATENT DOCUMENTS 5,258,021 A * 11/1993 Duran .................. A61F 2/2412
623/2.36
5,411,552 A    5/1995 Andersen et al.
(Continued)

FOREIGN PATENT DOCUMENTS

WO    WO 91/17720 A1    11/1991
WO    WO 2007/142935 A1    12/2007
(Continued)

OTHER PUBLICATIONS

International Search Report dated May 20, 2010 in International Application No. PCT/GB2010/000627.
(Continued)

*Primary Examiner* — Seema Mathew
(74) *Attorney, Agent, or Firm* — Fitch, Even, Tabin & Flannery, LLP

(57) ABSTRACT

A heart valve prosthesis comprising: a support structure comprising a framework deformable between an expanded state and a compressed state and vice versa; and a flow-control structure, supported by the support structure, for permitting blood flow in a first direction, and for restricting blood flow in a direction opposite to the first direction. At least one end of the support structure comprises a plurality of apexes of the framework. The support structure is collapsible into the compressed state by pulling on the apexes, to enable it to be drawn into a sheath having an inner radial dimension smaller than the radial dimension of the support structure in the expanded state.

8 Claims, 9 Drawing Sheets

(58) Field of Classification Search
USPC .................. 623/1.24, 1.26, 2.1, 2.12, 2.17
See application file for complete search history.

(56) References Cited

U.S. PATENT DOCUMENTS

| | | | | |
|---|---|---|---|---|
| 5,489,297 | A * | 2/1996 | Duran | A61F 2/2412 623/2.13 |
| 5,607,465 | A * | 3/1997 | Camilli | A61F 2/2418 604/104 |
| 5,855,601 | A * | 1/1999 | Bessler | A61B 17/32072 623/2.38 |
| 5,957,949 | A | 9/1999 | Leonhardt et al. | |
| 6,296,662 | B1 * | 10/2001 | Caffey | A61F 2/2418 623/2.14 |
| 6,425,916 | B1 | 7/2002 | Garrison et al. | |
| 6,440,164 | B1 | 8/2002 | DiMatteo et al. | |
| 6,635,085 | B1 * | 10/2003 | Caffey | A61F 2/2415 623/2.1 |
| 7,524,331 | B2 * | 4/2009 | Birdsall | A61F 2/2412 623/1.24 |
| 7,854,761 | B2 | 12/2010 | Richardson et al. | |
| 7,871,436 | B2 | 1/2011 | Ryan et al. | |
| 8,906,083 | B2 | 12/2014 | Obermiller et al. | |
| 9,044,318 | B2 | 6/2015 | Straubinger et al. | |
| 9,138,315 | B2 * | 9/2015 | Straubinger | A61F 2/2427 |
| 9,168,130 | B2 | 10/2015 | Straubinger et al. | |
| 9,180,030 | B2 * | 11/2015 | Brocker | A61F 2/07 |
| 9,301,843 | B2 | 4/2016 | Richardson et al. | |
| 2002/0055775 | A1 * | 5/2002 | Carpentier | A61F 2/2412 623/2.17 |
| 2004/0098112 | A1 | 5/2004 | DiMatteo et al. | |
| 2004/0117004 | A1 | 6/2004 | Osborne et al. | |
| 2004/0186563 | A1 * | 9/2004 | Lobbi | A61F 2/2418 623/2.11 |
| 2005/0075724 | A1 | 4/2005 | Svanidze et al. | |
| 2005/0137676 | A1 | 6/2005 | Richardson et al. | |
| 2005/0137690 | A1 | 6/2005 | Salahieh et al. | |
| 2006/0004436 | A1 * | 1/2006 | Amarant | A61F 2/88 623/1.15 |
| 2006/0259137 | A1 | 11/2006 | Artof et al. | |
| 2006/0265056 | A1 * | 11/2006 | Nguyen et al. | 623/2.18 |
| 2006/0271166 | A1 * | 11/2006 | Thill | A61F 2/2418 623/1.23 |
| 2007/0043435 | A1 * | 2/2007 | Seguin et al. | 623/2.11 |
| 2007/0067021 | A1 * | 3/2007 | Haverkost | A61F 2/2418 623/1.24 |
| 2007/0239265 | A1 | 10/2007 | Birdsall | |
| 2008/0133003 | A1 | 6/2008 | Sequin et al. | |
| 2008/0140189 | A1 * | 6/2008 | Nguyen | A61F 2/2412 623/2.11 |
| 2008/0228263 | A1 | 9/2008 | Ryan | |
| 2008/0234814 | A1 | 9/2008 | Salahieh et al. | |
| 2008/0255661 | A1 * | 10/2008 | Straubinger et al. | 623/2.36 |
| 2008/0269878 | A1 | 10/2008 | Iobbi | |
| 2009/0005863 | A1 * | 1/2009 | Goetz | A61F 2/2418 623/2.18 |
| 2009/0216310 | A1 | 8/2009 | Straubinger et al. | |
| 2009/0216313 | A1 | 8/2009 | Straubinger et al. | |
| 2014/0180390 | A1 * | 6/2014 | Havel | A61F 2/07 623/1.13 |

FOREIGN PATENT DOCUMENTS

| | | |
|---|---|---|
| WO | WO 2008/029296 A2 | 3/2008 |
| WO | WO 2008/070797 A2 | 6/2008 |
| WO | WO 2008/091493 A1 | 7/2008 |
| WO | WO 2009/029199 A1 | 3/2009 |
| WO | WO 2009/061389 A2 | 5/2009 |

OTHER PUBLICATIONS

Search Report from search dated Jul. 27, 2009 in British Application GB 0905444.6.
International Search Report issued in International Application PCT/GB2010/000627.
International Preliminary Examination Report issued in International Application PCT/GB2010/000627.
Third Party List of references.

* cited by examiner

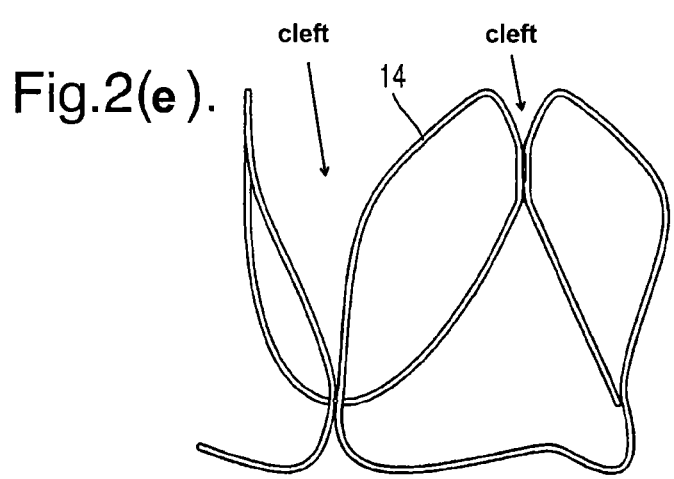

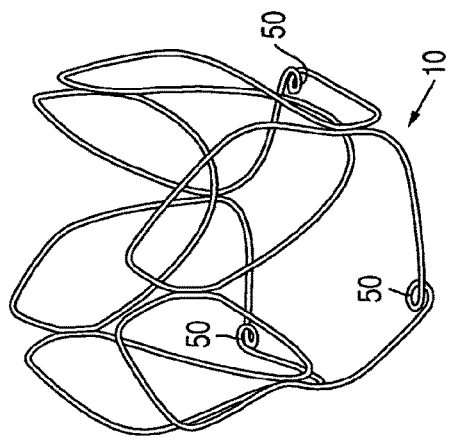
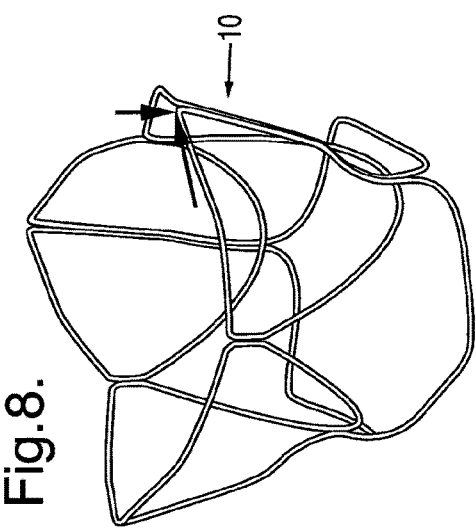
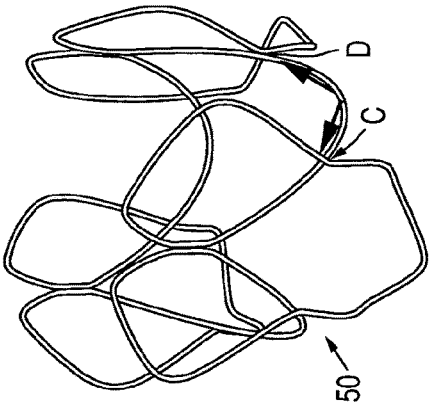
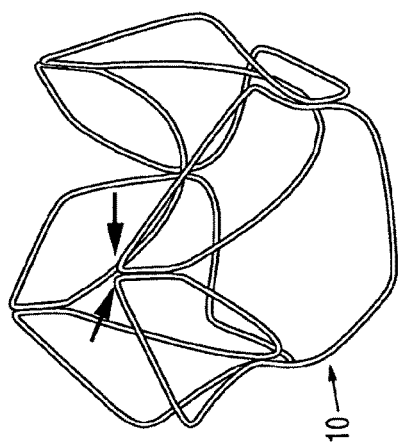
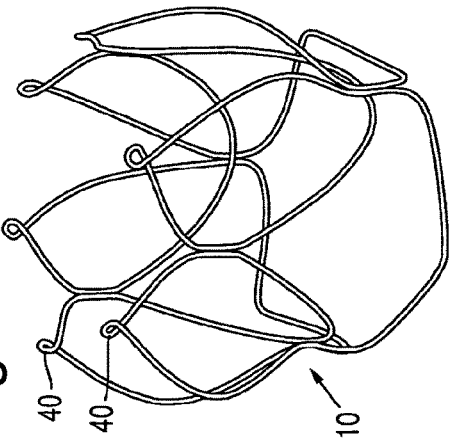

though the percutaneous implantation technique is ideally suited to use in a clinic, it generally has to be performed at a hospital or large facility that has full surgical operating theatres in the event of complications because the conventional prosthetic heart valve cannot be collapsed and removed endovascularly.

HEART VALVE PROSTHESIS

CROSS-REFERENCE TO RELATED APPLICATIONS

This is a U.S. National Phase of International Application PCT/GB2010/000627, filed Mar. 30, 2010, and claims the benefit of foreign priority from GB Patent Application 0905444.6, filed Mar. 30, 2009, the entire disclosures of which applications are hereby incorporated herein by reference.

The present invention relates to heart valve prostheses, namely implantable replacement heart valves. For brevity, in the following these will generally simply be referred to as "heart valves".

Prosthetic heart valves have been an area of considerable research in recent years. Typically, the heart valve comprises two elements: a support structure comprising a generally tubular framework surrounding a flow passage; and a flow control structure provided in the lumen of the support structure and providing the one-way valve action to permit blood flow in one direction through the valve, but preventing blood flow in the reverse direction.

In recent years percutaneous implantation of heart valves has been favoured. In this context, percutaneous refers to accessing the heart with a minimally invasive technique, as opposed to full open-heart surgery. Percutaneous techniques include endovascular implantation and thorasic-microsurgery. According to these techniques, access is done via needle-puncture of the skin, and does not require scalpel incisions to open the thoracic cavity and expose the heart.

For percutaneous delivery of a heart valve, the valve must be collapsible to a compressed state such that it can be delivered e.g. through the venous or arterial system using a catheter and guide wire, to the required position, and then expanded in situ into its normal operating state. In many cases known in the art, the support structure is essentially similar to a stent used for angioplasty.

However, there are a number of problems with conventional percutaneous prosthetic heart valves. One problem is achieving the desirable compactness in the compressed state, being both radially compact to fit within the lumen of the vascular system, and axially compact so as to pass round tortuous bends in the vascular system when being delivered to the heart. Another problem is with providing the heart valve with adequate anchoring to avoid displacement or migration of the valve from the implanted position. A further problem is with the support structure of the heart valve. Many conventional stents are manufactured from a metal tube out of which rhombus-shaped holes are laser-cut to leave an open lattice-like framework. The resulting device may have durability problems because material dishomogeneities may be set up when the initial tube is manufactured by a drawing process, and these can lead to cracks and failure of the structure.

Yet another problem is that the heart valve cannot be stored in its compressed state because this would result in damage to the flow control structure. Therefore, it must be collapsed to its compressed state shortly prior to implantation. This has logistical problems and may require expensive crimping devices and skilled personnel to be on hand to compress the prosthetic heart valve.

Another problem with conventional prosthetic heart valves is that it is difficult or impossible to retrieve them back into the catheter sleeve or sheath after they have been released. This might be necessary in case of incorrect positioning or other complications during the implantation procedure. This has been a significant disadvantage because although the percutaneous implantation technique is ideally suited to use in a clinic, it generally has to be performed at a hospital or large facility that has full surgical operating theatres in the event of complications because the conventional prosthetic heart valve cannot be collapsed and removed endovascularly.

A further problem is that in heart valves in which the flow control structure comprises flaps, also known as leaflets, the support structure is not configured to provide ideal support for the peripheral edge of the leaflets.

The present invention seeks to alleviate, at least partially, some or any of the above problems.

The present invention provides: a heart valve prosthesis comprising:

a support structure comprising a framework deformable between an expanded state and a compressed state and vice versa; and a flow-control structure, supported by the support structure, for permitting blood flow in a first direction, defining an axial direction of the prosthesis, and for restricting blood flow in a direction opposite to the first direction, wherein at least one end of the support structure comprises a plurality of apexes of the framework, and wherein the support structure is collapsible into the compressed state by pulling on the apexes, to enable it to be drawn into a sheath in the compressed state, the sheath having an inner radial dimension smaller than the radial dimension of the support structure in the expanded state.

Another aspect of the invention provides: a method of collapsing a heart valve prosthesis, the prosthesis comprising:

a support structure comprising a framework deformable between an expanded state and a compressed state and vice versa; and a flow-control structure, supported by the support structure, for permitting blood flow in a first direction, defining an axial direction of the prosthesis, and for restricting blood flow in a direction opposite to the first direction, wherein at least one end of the support structure comprises a plurality of apexes of the framework, the method comprising:

pulling on the apexes when in the expanded state, to commence collapse into the compressed state; and drawing the prosthesis into a sheath having an inner radial dimension smaller than the radial dimension of the support structure in the expanded state.

Embodiments of the invention will now be described, by way of example only, with reference to the accompanying drawings in which:

FIGS. 1(a) to 1(d) are views of the heart valve according to a first embodiment of the invention;

FIGS. 2(a) to 2(d) are the same views of the first embodiment of the device as in FIG. 1, but with the flow control structure removed for clarity;

Figure 12A:
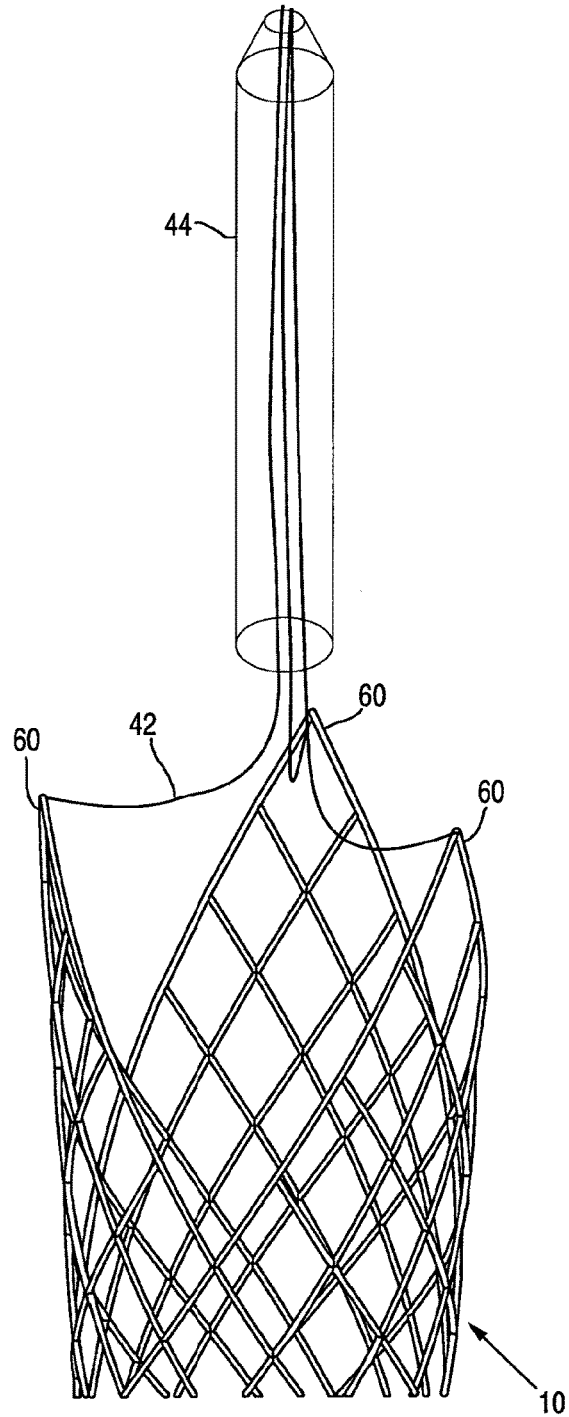
Figure 12B:
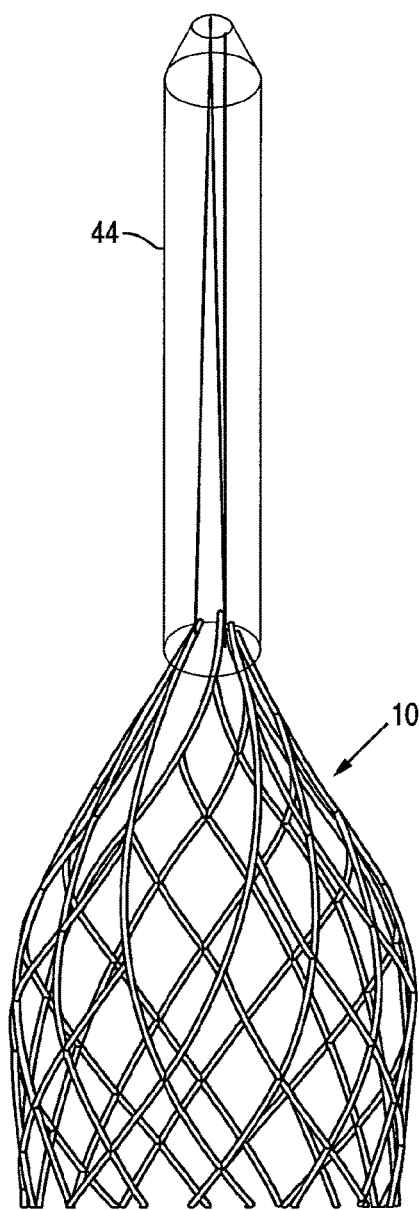

FIGS. 4(a) to 4(d) show views of a heart valve according to a second embodiment of the invention;

FIGS. 5(a) to 5(d) show the heart valve of the second embodiment with the flow control structure removed for clarity;

FIGS. 6(a) to 6(d) show the sequence of retrieving the heart valve of the second embodiment back into the sheath;

FIGS. 7 to 10 show further embodiments of the support structure of the heart valve that are modifications of the first and second embodiments;

FIG. 11 illustrates an embodiment in which the loops are positioned to be inward facing; and FIG. 12 illustrates a further embodiment of the invention.

As explained previously, the prosthetic heart valve comprises a support structure and a flow control structure. In the accompanying figures, the flow control structure is only illustrated in FIGS. 1, 3 and 4; in the rest of the figures the flow control structure is omitted purely for illustrative purposes to assist in showing the support structure more clearly. The final device would, of course, include the flow control structure.

In the following description, references to the top, bottom, side, upper, lower and so forth simply refer to the orientation of the device shown in the figures, and do not necessarily bear any relation to the final orientation of the device when implanted. The flow direction of the heart valve shown in the figures is generally in a direction from the bottom to the top in the orientation of the device shown in most of the figures, but these labels "bottom" and "top" merely refer to the orientation of the device as illustrated.

Referring to FIG. 1, the heart valve according to this first embodiment of the invention comprises a support structure 10 and a flow control structure 12. FIGS. 1(a) and 1(b) are side views of the heart valve. Because these figures are orthographic projections, and FIG. 1(a) is viewed perpendicular to a mirror plane of the heart valve, only the front half of the structure is visible in FIG. 1(a). FIG. 1(b) is a side view of the heart valve rotated 30° with respect to FIG. 1(a). FIG. 1(c) is an axial view from above with respect to FIG. 1(a). FIG. 1(d) is a view from above and to one side of the heart valve. In FIG. 1, the flow control structure 12 is shown semi-transparent for clarity to enable portions of the structure behind it to be seen.

The support structure 10 defines an approximately cylindrical cage defining a flow passage, and the axis of the cylinder is aligned with the blood flow direction through the valve.

The support structure 10 comprises a plurality of ribs 14. In the preferred embodiment, the ribs 14 are made from metal wire, preferably of shape memory metal or superelastic materials, such as nickel-titanium alloys known in the art as Nitinol; however, they may be made of other materials, such as stainless steel or other deformable materials that are biocompatible or can be made biocompatible.

As shown in FIG. 1, the support structure 10 can be formed by bending wire ribs 14 into curved arcs to provide the open framework. In fact, as illustrated, the entire support structure 10 can be made from a single wire that is bent into the appropriate shape. The starting wire could be a loop or could be a straight wire; if a straight wire, the two free ends may optionally be joined together. Alternatively, two or more wires may be used, or the support structure 10 can be formed by laser-cutting out the wall of a tube and then forming into shape. After the support structure 10 has been formed into the desired shape, further fabrication steps may be performed. For example, in FIG. 1(a), the ribs 14 are joined at points A and B, for example by welding, soldering or crimping. Furthermore, appropriate heat treatment as is well known in the art, may be applied, if necessary, to achieve the desired elastic properties of the support structure 10 such that it can be collapsed into a compressed state, as described further below, and then elastically self-expand to the state shown in FIG. 1 and resiliently engage against the native anatomy at the location in which it is implanted.

Figure 1B:
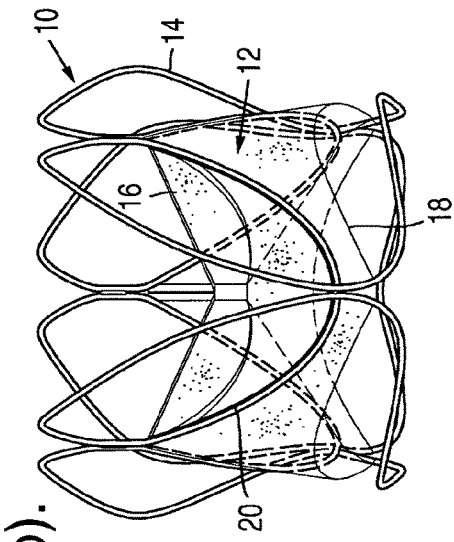
Figure 1D:
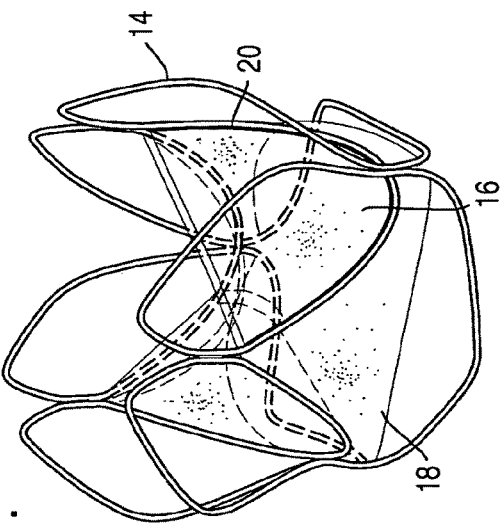
Figure 1A:
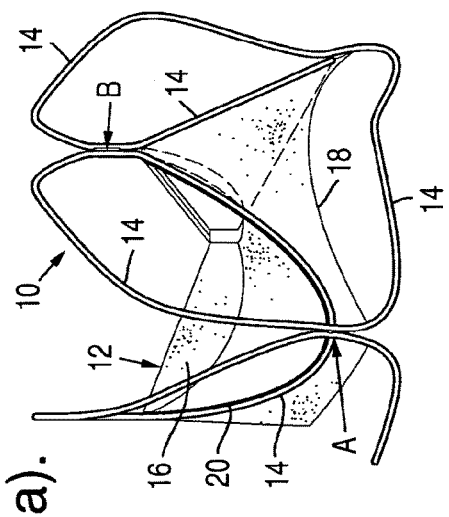
Figure 1C:
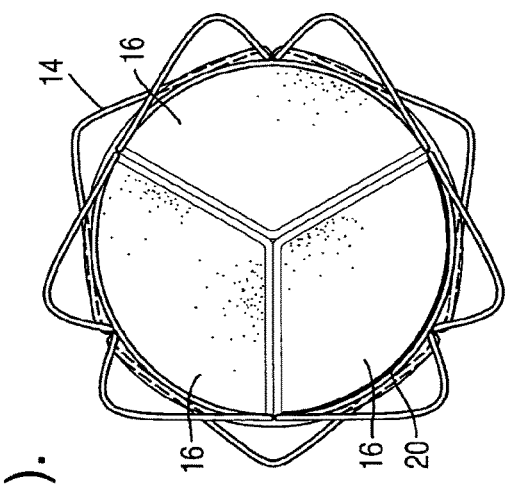
Figure 2B:
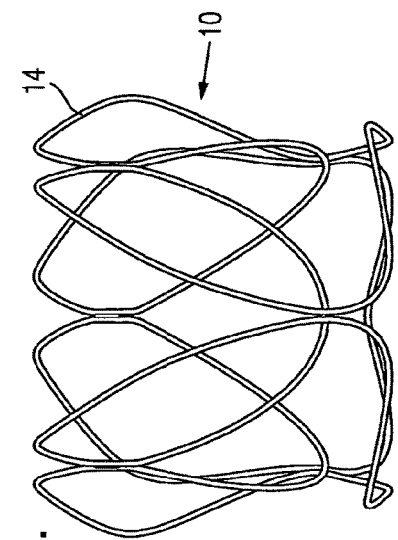
FIG. 2(e) is a view of an embodiment of the device as in FIG. 2 (a) and FIG. 1 in which clefts are indicated, but with the flow control structure removed for clarity.
Figure 2D:
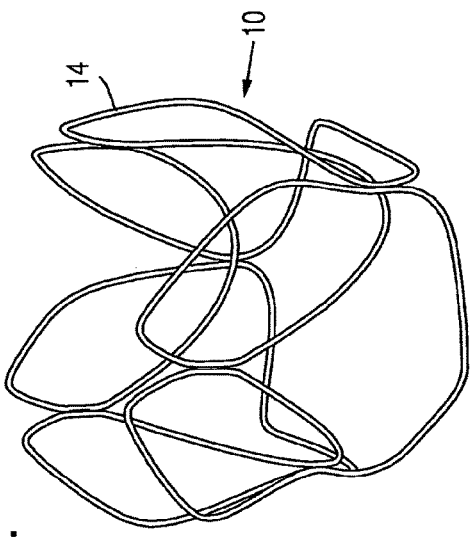
Figure 2A:
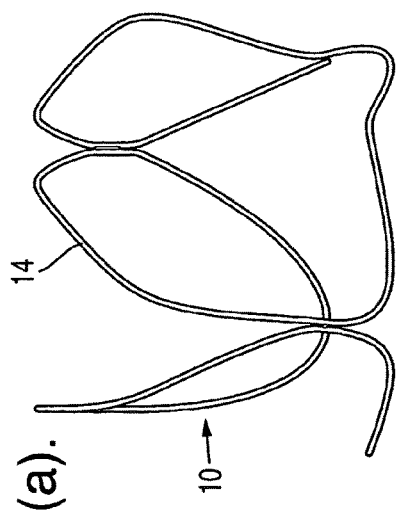
Figure 2C:
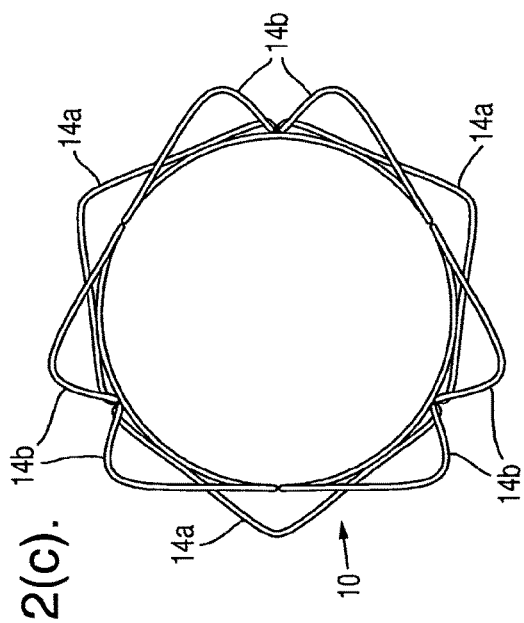

As can be seen in FIG. 1(c), the support structure 10 defines a generally circular region when viewed axially in which the flow control structure 12 is situated. As can be seen from FIGS. 1 and 2, the flow control structure 12 is located in the region of smallest diameter of the support structure 10 where it defines a waist. Above and below the flow control structure 12, the ribs 14 of the support structure 10 are curved to define generally petal-like shapes, which will simply be referred to as petals; the periphery of these petals being defined by the ribs 14. The petals formed by the ribs 14 protrude radially both above and below the middle waist region, and comprise two sets of petals, to clamp the structure in position. The protrusion of the petals can be most clearly seen in FIGS. 1(c) and 2(c). The petals of the first set of petals protrude below the flow control structure 12 at the waist region, and are indicated 14a in FIG. 2(c), and the petals of the second set of petals protrude above the flow control structure 12 at the waist region, and are indicated 14b in FIG. 2(c). In this specific embodiment there are six petal protrusions above the waist region and three petal protrusions below the waist region.

The ribs 14 are curved in smooth arcs and define a very open structure. This alleviates disturbance to the blood flow and lessens the impact on surrounding tissue; it also is less susceptible to thrombogenesis.

Regarding the flow control structure 12, in this embodiment it comprises three leaflets 16. The commissures along which adjacent leaflets 16 meet form a Y-shape as can be seen in FIG. 1(c). In the accompanying drawings, the valve is shown in the closed position. When there is an excess of blood pressure below the leaflets 16, they flex back and the commissures part to allow blood to flow through. Blood is prevented from flowing in the reverse direction because an excess of pressure from above simply tends to force the leaflets together into the closed position in which the flow passage is occluded. As well as the leaflets 16, the flow control structure also comprises a skirt 18 that defines the flow passage.

The flow control structure of this embodiment or any of the other embodiments can be entirely synthetic, for example formed from artificial polymeric material, or can be biologically-derived, for example a xenograft of bovine pericardium or porcine pericardium, or a combination of synthetic and biologically-derived.

In FIGS. 1(a) to 1(d), the radially outward peripheral edge 20 of one of the leaflets 16 has been indicated with a thick dark line for emphasis. As can be seen, a rib 14 of the support structure 10 closely follows the edge 20. This enables the leaflets 16 to be attached to the support structure 10 along the ideal support line, and without requiring additional members to be provided in the support structure 10. The leaflet edge 20 can be attached to the rib 14 for example by suturing or gluing.

Figure 3:
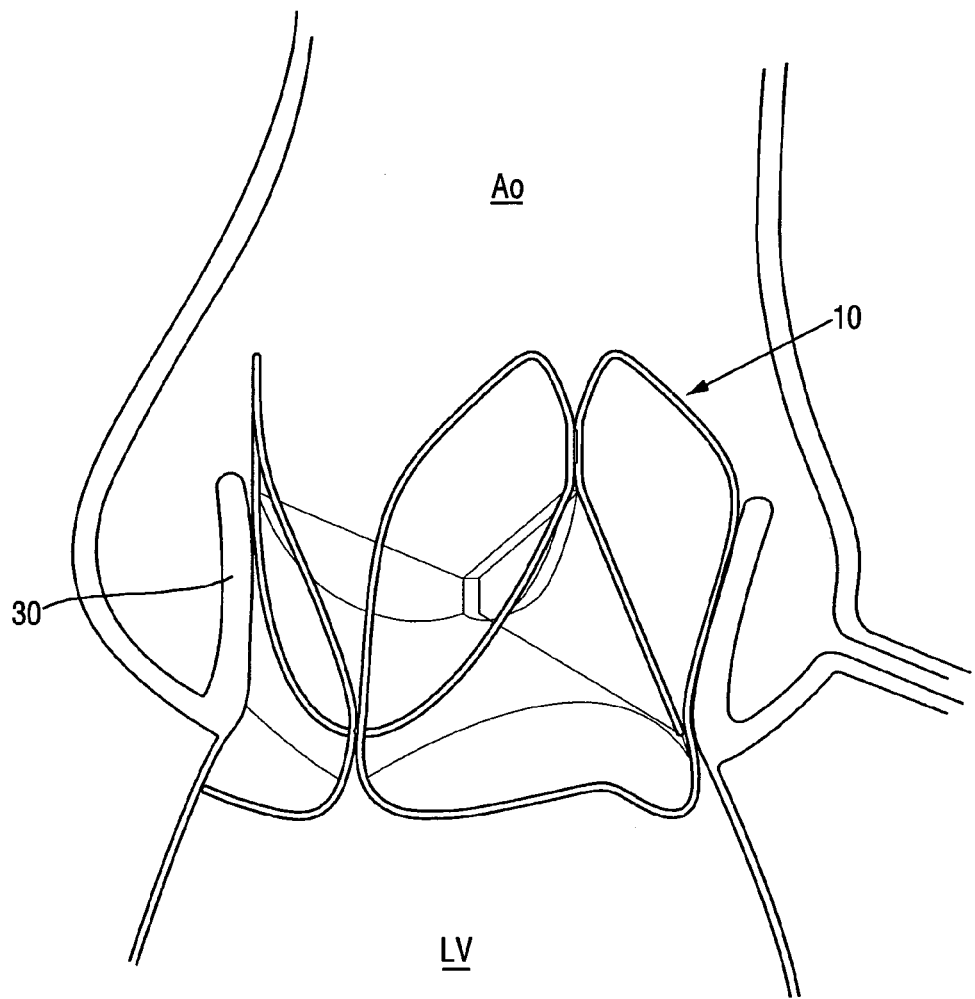
FIG. 3 illustrates the heart valve of the first embodiment implanted at the location of the aortic valve.
Figure 4B:
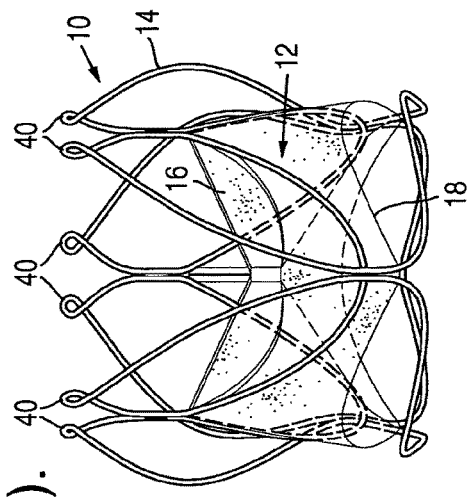
Figure 4D:
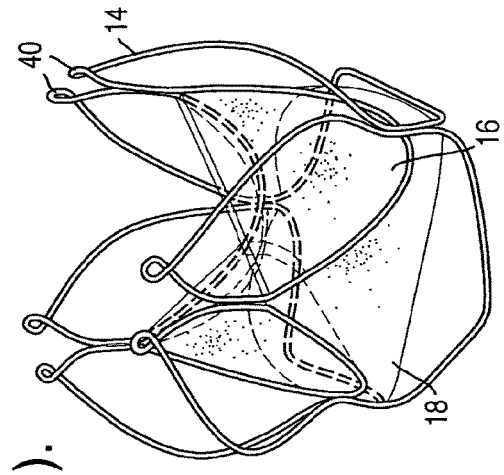
Figure 4A:
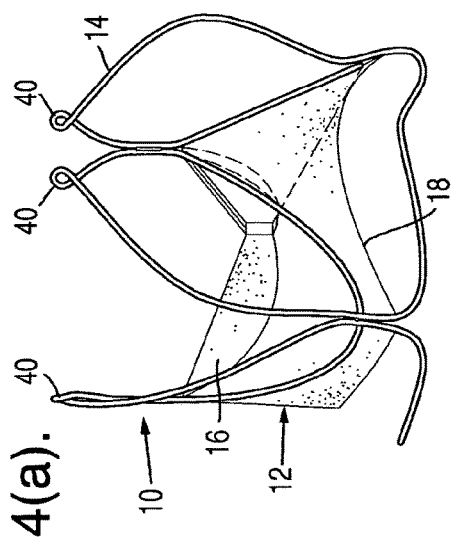
Figure 4C:
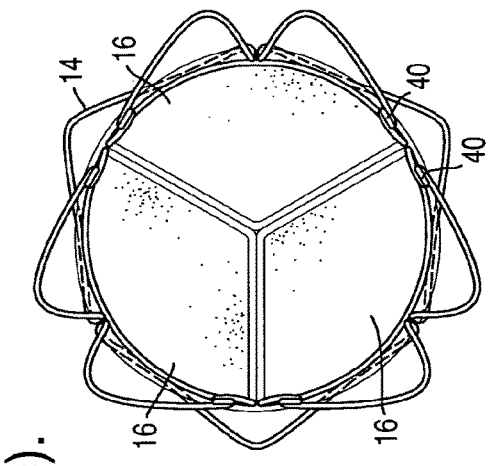
Figure 5B:
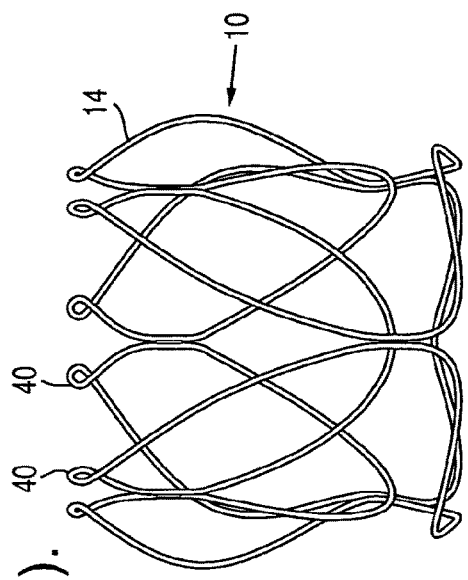
Figure 5D:
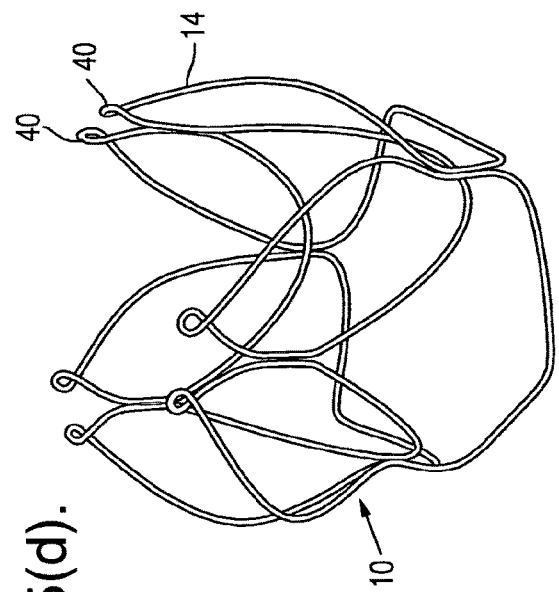
Figure 5A:
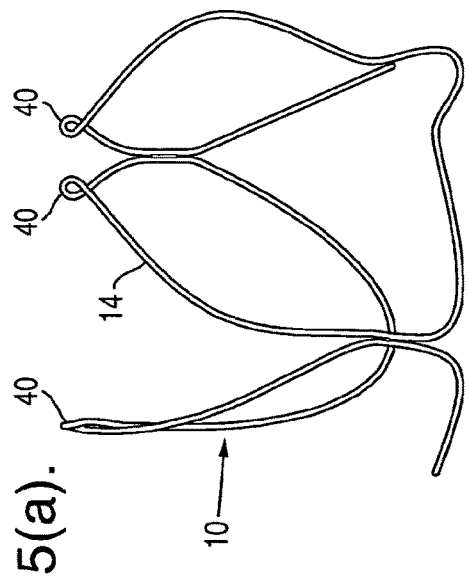
Figure 5C:
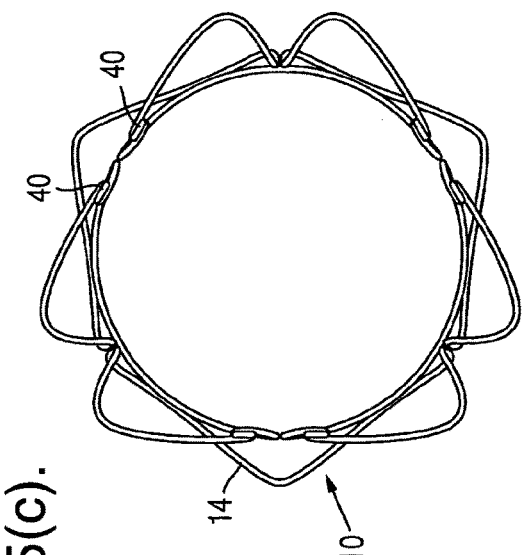
Figure 6D:
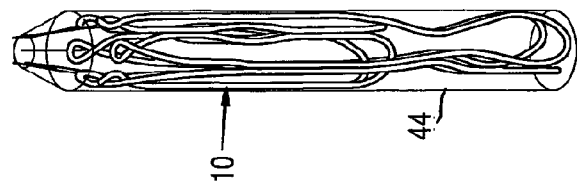
Figure 6C:
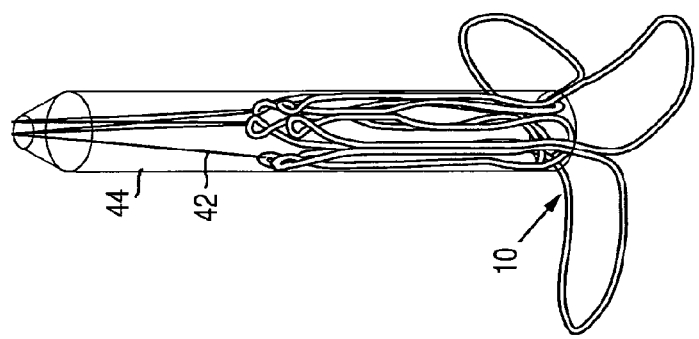
Figure 6B:
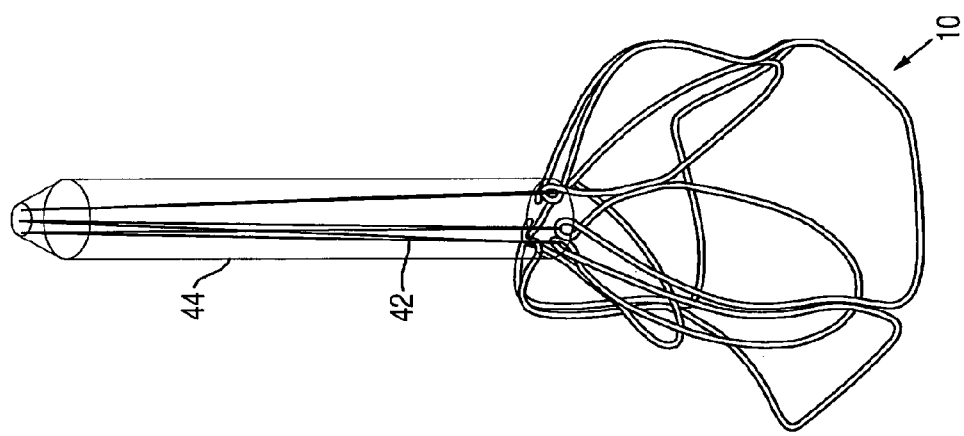
Figure 6A:
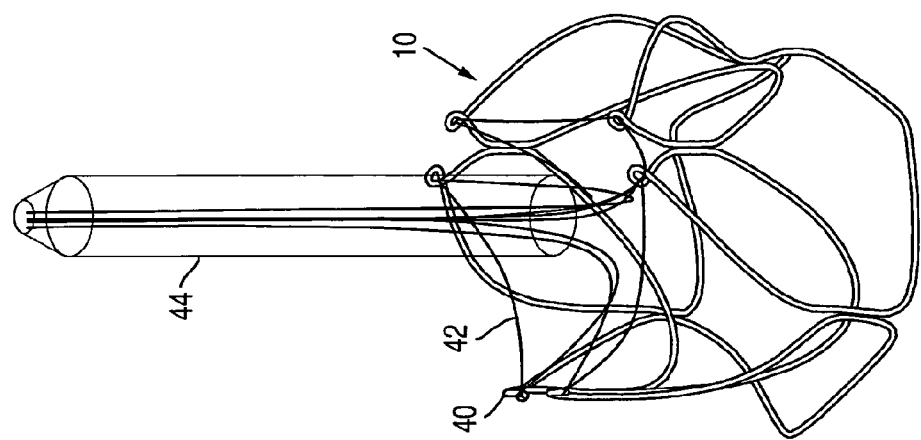

FIG. 3 shows schematically the heart valve of the first embodiment when implanted as an aortic valve. The lower petal protrusions project into the left ventricle LV and the upper petal protrusions project radially in the region of the root of the aorta Ao. The native leaflets 30 of the aortic valve are displaced and fit in the waist region of the prosthetic heart valve. This wedges the prosthetic heart valve in place such that it is secure and cannot be displaced in either axial direction.

The heart valve of this and other embodiments can be implanted by retrograde access or antegrade access. In both cases, the heart valve is collapsed to a compressed state, discussed further below, and held within a sheath on the end of a guide wire that is inserted into the vascular system through a catheter. With retrograde access, the catheter is inserted into an artery, for example a femoral artery, and the heart valve is conveyed in the direction opposite to the blood flow to the aorta and is withdrawn from the sheath at the position of the aortic valve. In antegrade access, a catheter is inserted in a vein, such as a femoral vein, and passed through the venous system in the same direction as the blood flow to the right atrium, then the inter-atrial septum is punctured and the heart valve is passed into the left atrium, then the left ventricle and then to the position of the aortic valve. The heart valve can, of course, be implanted by other surgical techniques.

Although the specific embodiment illustrated in FIG. 3 is an aortic valve replacement, embodiments of the invention can equally be applied to other heart valves, such as the pulmonary valve, the mitral valve or the tricuspid valve. Again, these may be delivered by retrograde access or antegrade access according to the circumstances.

A second embodiment of the invention will now be described with reference to FIGS. 4 and 5. Most of the details are identical to the first embodiment, so will not be described again to avoid repetition. The difference with this second embodiment is that the apexes of the petal-like shapes formed by the ribs 14 of the support structure 10 are formed into loops 40 at the upper end of the device. These loops 40 have several functions. One is to enable a filiform material to be attached securely to pull on the device to enable it to be collapsed and/or retrieved, as will be described further below. Another function is that when the support structure is formed from bent wire as illustrated in FIG. 4, then the loops 40 act as torsion springs that reduce the bending stresses acting on the support structure when the valve is collapsed and assist in self-expanding the heart valve to its expanded state.

Referring to FIG. 6, this shows a sequence of snapshots of collapsing the heart valve into a compressed state. In FIG. 6(a), loops of filiform material 42 pass through pairs of adjacent loops 40 of the support structure 10. The threads of filiform material 42 pass out through a sheath 44. When the filiform material is pulled, the loops 40 are gathered together as shown in FIG. 6(b), and then the upper petal-like shapes collapse and can be withdrawn into the sheath 44 as shown in FIG. 6(c). In this state, the lower petal-like shapes have also become folded. On further pulling of the filiform material, the structure is completely withdrawn into the sheath 44 as shown in FIG. 6(d).

The operation shown in FIG. 6 can be easily performed ex vivo immediately prior to implanting the heart valve, and does not require any specialist crimping apparatus or expertise.

When the sheath 44 has been delivered, for example endovascularly on the end of a guide wire to the required implantation position, the reverse sequence of FIG. 6 is performed and the sheath 44 is withdrawn away from the heart valve structure. The lower petal-like protrusions expand first as shown in FIG. 6(c) and enable the heart valve to be initially correctly positioned, including rotational positioning. Further withdrawal of the sheath 44 allows the heart valve to self-expand as shown in FIGS. 6(b) and 6(a). In the event that the heart valve needs to be repositioned or retrieved entirely, the filiform material 42 can be pulled again to collapse the structure into its compressed state, either partially or fully. When the positioning is finalised, the filiform material 42 and the sheath 44 can be completely withdrawn via the reverse route through which access was obtained.

Although it is preferred, as in the second embodiment, to have loops 40 for attaching a filiform material for pulling on the support structure 10, other attachment shapes are possible, including simply using the apexes of the petal-like portions. Furthermore, it is not necessarily required to use filiform material attached to the support structure; instead an arrangement using hooks and a different form of sheath could be used. However, the loops 40 can be advantageous because they facilitate circumferential pulling of the apexes towards each other and not just axially or radially pulling.

In a further variant, the prosthesis can be provided with a loop of filiform material attached to the apexes at one end of the support structure, for example by passing through each of the loops 40 of FIG. 5. The prosthesis can be delivered and withdrawn from the sheath such that it is fully expanded. The loop of filiform material is dimensioned such that in the expanded state of the structure it forms a ring of approximately the same diameter as the prosthesis so that it does not interfer with the flow through the valve. However, if it is required to collapse the structure, one or more hooks, on guidewire inserted through a catheter, can be used to catch on to the loop of filiform material and then pull on it such that the apexes are drawn together radially. In this way, the loop of filiform material acts like a purse-string. The apexes are also pulled axially so that the structure can be drawn into a sheath for removal percutaneously, without requiring significant surgical access.

Further embodiments of the invention will now be described with reference to FIGS. 7 to 11. These are generally modifications of the previous embodiments and can, of course, be used in any appropriate combination with each other and/or the previous embodiments. Description of features already described will not be repeated.

FIG. 7 shows an arrangement in which adjacent pairs of apexes are brought together (as indicated by the arrows for one of the pairs). By comparison with FIG. 1(d), it can be seen that these pairs of adjacent apexes are aligned with the commissures between the valve leaflets.

FIG. 8 shows a different arrangement in which neighbouring apexes in the opposite sense to FIG. 7 are brought together (as indicated by the arrows for one pair). In this case the apex pairs are aligned with the centre of their newest leaflet.

FIG. 9 shows an arrangement in which the apexes are equally spaced apart in the circumferential sense around the axis of the heart valve.

FIG. 1(a) showed an arrangement in which three ribs 14 met at a point A that coincided with the centre of the outer peripheral edge of a leaflet 16. In the arrangement according to FIG. 10, by comparison, the ribs meet at two points C and D that are separated from the centre of the leaflets.

In the embodiment of FIG. 11, loops 50 are formed at the apex of each lower protrusion of the support structure 10. This is particular applicable for the case in which the valve is withdrawn into a sheath in the opposite direction to that shown in FIG. 6 and is advantageous when the heart valve is to be implanted by antegrade access. As shown in FIG. 11, the loops 50 are preferably positioned to be inward facing to avoid damage to surrounding tissue.

FIG. 12 illustrates another embodiment of the invention. In this case, the support structure 10 is formed of a generally tubular mesh, as known from the field of stents. However, in this case, the end of the support structure illustrated in FIG. 12(a) is not a complete cylinder, but comprises regions that each come to an apex 60 and there are gaps between the apexes. In this way, when filiform material is attached to the apexes 60 and pulled, the structure can be readily collapsed and withdrawn into a sheath 44 as shown in FIG. 12(*b*). If a cylindrical mesh-like structure (without apexes and gaps in between) is attempted to be collapsed in the same way, then its wall simply buckles and it cannot be successfully radially compressed and withdrawn into a sheath.

As can be seen in many of the above embodiments, including those in FIGS. 1 to 6 and 12, to enable the heart valve to be collapsible, the end of the support structure at which the collapsing is to begin is a relatively open structure with projecting portions having apexes that can be pulled together, and in between the apexes there are large gaps or clefts. Preferably the length of the clefts in the axial direction is greater than the average radius of the support structure, and more preferably the cleft length is greater than the average diameter of the support structure. Not all of the clefts have to be of this depth (length), but preferably there are at least three deep clefts that extend in the axial direction by a distance greater than or equal to the radius or greater than or equal to the diameter of the support structure.

The average diameter of the heart valve when in the expanded state is preferably in the range of from 15 to 32 mm, more preferably from 22 to 26 mm. These dimensions refer to the diameter of the flow-control structure 12; the maximum diameter, including protruding ribs 14, can go up to 40 mm. In the presently preferred embodiment, the maximum diameter is approximately 34 mm. The diameter of the heart valve when in the compressed state is preferably less than 10 mm, and more preferably less than 8 mm. The axial length of the heart valve in the expanded state is preferably in the range of from 15 to 40 mm, more preferably from 22 to 30 mm. When in the radially compressed state, the axial length occupied by the heart valve is increased relative to its expanded state because of the way that the structure folds, however the increase in axial length is less than 100%, preferably less than 80%, and can be as little as 20%.

In the embodiments described above, the heart valve has three-fold rotational symmetry about the axis parallel to the flow direction. However, this is merely one example that corresponds approximately with the aortic valve physiology. Other numbers and spatial distributions of the apexes of the support structure are, of course, possible. Similarly, different numbers of valve leaflets 16 are contemplated, such as 2, 4 or more. The heart valve also need not be rotationally symmetric. Furthermore, other flow control structures, apart from leaflets, could be employed, such as discs or balls or other functionally equivalent structures known in the art.

The ribs 14 shown in the figures illustrating the specific embodiments described above generally define smooth arcs. However, it is also envisaged that at least some of the ribs 14 or portions thereof may not define monotonic curves, but may be wavy or sinusoidal or serpentine.

The invention claimed is:

1. A heart valve prosthesis comprising:
   a support structure comprising a framework deformable between an expanded state and a compressed state and vice versa, said support structure having a radial dimension when in the expanded state and a smaller radial dimension when in the compressed state, said support structure comprising smoothly curved ribs; and
   a flow-control structure, supported by the support structure, for permitting blood flow downstream in a first direction, defining an axial direction of the prosthesis, and for restricting blood flow in an upstream direction opposite to the first direction,
   wherein the flow-control structure comprises at least three leaflets each having a radially outer edge so as to define a profile, each leaflet having an associated smoothly curved rib,
   each associated smoothly curved rib having a curve to match the profile of the radially outer edge of their associated leaflet and to which each said individual smoothly curved rib is attached,
   wherein the support structure further comprises a first set of petal-like portions that protrude beyond the flow-control structure axially in the upstream direction in which the flow-control structure restricts blood flow opposite to the first direction in which the flow-control structure permits blood flow, and protrude radially further than the flow-control structure,
   wherein at least one end of the support structure comprises a plurality of apexes of the framework,
   wherein the support structure is collapsible from the fully expanded state into the compressed state by pulling on the apexes, to enable it to be drawn into a sheath in the compressed state, the sheath having an inner radial dimension smaller than the radial dimension of the support structure in the expanded state, and
   wherein the smoothly curved ribs are a single bent wire.

2. A prosthesis according to claim 1, wherein the support structure comprises a second set of petal-like portions that protrude beyond the flow-control structure axially in the downstream first direction, and protrude radially further than the flow-control structure.

3. A prosthesis according to claim 2, wherein the first set of petal-like portions and the second set of petal-like portions are configured so as to clamp the structure in position.

4. A prosthesis according to claim 1, wherein loops are provided at the apexes for attaching members for pulling thereon for collapsing the heart valve.

5. A prosthesis according to claim 1, further comprising clefts in the support structure between apexes, wherein at least one of the clefts is a deep cleft having a length in the axial direction greater than the average radius of the support structure.

6. A prosthesis according to claim 5, wherein the length in the axial direction of the deep cleft is greater than the average diameter of the support structure.

7. A prosthesis according to claim 5, comprising at least three deep clefts.

8. A prosthesis according to claim 1, wherein the support structure is elastically deformable, and is self-expanding from the compressed state to the expanded state.

\* \* \* \* \*